United States Patent [19]
Hagiwara et al.

[11] Patent Number: 5,602,027
[45] Date of Patent: Feb. 11, 1997

[54] CELL LINE TRIH8 OBTAINED BY THE FUSION OF THE HUMAN EPIDERMOID CARCINOMA CELL LINE A431 WITH THE TOS/H8 HYBRIDOMA

[75] Inventors: Hideaki Hagiwara, Takarazuka; Hideo Yuasa, Kasai, both of Japan

[73] Assignee: Yoshihide Hagiwara, Takarazuka, Japan

[21] Appl. No.: 991,596

[22] Filed: Dec. 16, 1992

[30] Foreign Application Priority Data

Dec. 25, 1991 [JP] Japan ................................ 3-356551

[51] Int. Cl.$^6$ ................................ C12N 5/12; C12N 5/24
[52] U.S. Cl. .................................. 435/344; 435/346
[58] Field of Search ..................... 435/240.26, 240.27, 435/240.31, 172.2, 70.2

[56] References Cited

U.S. PATENT DOCUMENTS 4,757,018   7/1988   Brown .

FOREIGN PATENT DOCUMENTS 0062409   10/1982   European Pat. Off. .
0307247   3/1989   European Pat. Off. .
WO8705929   10/1987   WIPO .

OTHER PUBLICATIONS

Okabe, et al.; Cancer Research, vol. 46, pp. 1043–1046; 1986.
Masuda, et al.; In Vitro Cellular & Developmental Biology, vol. 24, No. 9, pp. 893–899; 1988.
Tarleton, et al.; BioTechniques, vol. 11, No. 5, pp. 590–593; 1991.
Hoffman, et al., 92–05273, Biotechnology Abstracts, 1991.
Keay, et al., 89–07550, Biotech. Abstracts, 1989.
Aotsuka et al. Cell Immunol. 133(2):498–505 (1991).
Hagiwara et al. J. Immunol Methods 135(1–2):263–271 (1990).

*Primary Examiner*—Donald E. Adams
*Attorney, Agent, or Firm*—Sherman and Shalloway

[57] ABSTRACT

A new cell line TriH8 is obtained by fusing a particular sub-clone, A431c, of the human epidermoid carcinoma cell line A431 with the TOS/H8 (human/human) hybridoma. Fused cell TriH8 has been deposited under FRI accession number FERM BP-4452. The fused cell is capable of proliferating in basal medium without addition of serum or growth factor. The cell line is more effective in producing antibody (IgM) than the donor cell TOS/H8.

1 Claim, 3 Drawing Sheets

CELL LINE TRIH8 OBTAINED BY THE FUSION OF THE HUMAN EPIDERMOID CARCINOMA CELL LINE A431 WITH THE TOS/H8 HYBRIDOMA

This invention relates to a method for obtaining particularly a fused cell, and more, relates to a method for obtention of a fused cell having an ability to produce a useful physiologically active substance of any kind such as a carcinostatically active substance, interferon, interleukin, TNF, CSF or a monoclonal antibody and capable of proliferating in a basal medium.

Various physiologically active substances useful for human beings such as carcinostatically active substances, immunopotentiating substances, interferon, interleukin, TNF, CSF and monoclonal antibodies are usually produced using human established cells. In culturing such an established cell line, generally, a complete cell culture medium comprising a basal medium having added thereto calf serum of the order of 5 to 10% (v/v) or a complete cell culture medium comprising a basal medium having added thereto a peptidic growth factor such as insulin or transferrin is used.

However, in a method for culturing of an established using such a complete cell culture medium, there are problems, for example, that the cost for production of a useful physiologically active substance increases because of use of expensive calf serum or growth factor, and/or the scatter of the production quantity of the useful physiologically active substance per lot enlarges, and the useful physiologically active substance is contaminated with heterogeneous proteins, and thus such a method is not suitable for culture on an industrial scale.

Thus, the present inventors thought that if a cell line having a useful physiologically active substance-producing ability in a basal medium not necessitating addition of calf serum or growth factor was cultured, the above problems could be overcome, and undertook research for obtaining useful substance-producing cells capable of proliferating in basal media.

As a result, they found that the above object could be accomplished by fusing an animal cell capable of proliferating in a basal medium with an animal cell having an ability to produce a desired useful physiologically active substance and substantially not proliferating in the basal medium, and completed this invention.

Thus, according to this invention there is provided a method for obtaining a fused cell having a useful substance-producing ability and capable of proliferating in a basal medium which comprises fusing (a) an animal cell capable of proliferating in the basal medium with, (b) an animal cell having the useful substance-producing ability and proliferating in a complete medium but substantially not proliferating in the basal medium, and recovering a fused cell clone having the useful substance-producing ability and capable of proliferating in the basal medium.

The method of this invention is described in more detail below.

In this specification, the "basal medium" is a medium which contains amino acids, salts, saccharides, vitamins, microelements, etc. and has, for culturing an animal cell, nutrients necessary for keeping the cell alive at the lowest level. For example, are mentioned Basal Medium Eagle, MEM-Dulbecco, L-15 Medium, McCoy 5A Medium, RPMI 1640 Medium, Ham's Medium F-12, etc. Further, a medium obtained by mixing some of them in an appropriate rate is included in the basal medium, too. For example, DF Medium obtained by mixing MEM-Dulbecco with Ham's Medium F-12 in 1:1 is mentioned.

Further, the "complete medium" is a medium comprising a basal medium having added thereto nutrients necessary for proliferation and expression of functions of each cell, and representatively mentioned is one obtained by adding fetal bovine serum in a quantity of the order of 10% (v/v). Further, the complete medium includes a serum-free medium which comprises a basal medium having added thereto, in place of serum, a carrier protein such as albumin or transferrin; a hormone such as insulin or asteroid hormone; a cell growth factor such as EGF; an extra-cellular matrix substance such as collagen or fibronectin, or the like and wherein expression of the proliferating function of each cell is made possible.

Further "useful substances" include substances produced by cells and having a physiological activity important in an animal species including human being, and for example, are mentioned a hematopoietic factor erythropoietin, TPA (tissue plasminogen activator) having a thrombolytic action, interferon said to be effective in some kind of carcinoma, a monoclonal antibody reacting with a specific antigen, an interleukin activating human lymphocytes, CSF stimulating proliferation of leukocytes (colony stimulating factors), etc.

The main characteristics of the method of this invention lie, as stated above, in fusing (a) an animal cell capable of proliferating in a basal medium [hereafter referred to as animal cell (a)] with (b) an animal cell having a useful substance-producing ability and proliferating in a complete medium but substantially not proliferating in the basal medium [hereafter referred to as animal cell (b)].

The animal cell (a) includes such a kind of cell strain that has an ability to secrete a growth factor necessary for self-proliferation, intracellularly or extracellularly, so-called an autocrinal property, and for example, are mentioned A431 (human epidermoid carcinoma), HeLa-P3 (human cervix carcinoma), HuL-1-P3 (human germinal liver), MDCK-P3 (canine liver), MDBK-P3 (bovine liver), L-P3 (murine embryo), JTC-21-P3 (rat liver), JTC-25-P3 (rat liver), JTC-16-P3 (rat hepatoma), RSP-2-P3 (rat spleen), human erythroleukemia-derived cell strain K-562, etc. [In the above the words in the parentheses mean cell sources (species, tissue)].

In this specification, the word "animal cell" is used in such a meaning that it includes not only a cell itself recovered from the animal but a cell created by recombining and/or fusing the cell using a gene manipulation technique.

There is no particular limitation about the animal cell (b) fused with the above animal cell (a) so long as, as stated above, it has a useful substance-producing ability, and proliferates in a complete medium and preferably can be permanently subcultured but does not substantially proliferate in a basal medium, and thus the animal cell (b) can be one of any kind, but, usually, it is desirable that it has at least one selective marker, for example antibiotic resistance. As specific examples of such an animal cell (b), there can be mentioned BALL-1 cell having an interferon α-producing ability, NAMALWA cell having an interferon α-producing ability, TOS/H8 hybridoma having an ability to produce the IgM monoclonal antibody having an ability to bind to cell strains derived from various cancer cells; THP-1 cell or U-937 cell having an interleukin (IL)-1-producing ability; Jurkat cell or HuT-78 cell having an IL-2-producing ability; Mo cell having an ability to produce CSF, IL-2 and interferon; etc.

The fusion of the animal cell (a) with the animal cell (b) can be carried out by a method known per se, for example a method disclosed in a literature such as Hideaki Hagiwara and Junzo Nagao, J. Immunol. Methods, 135, 263–271 (1990).

For example, a fusing operation can be carried out by contacting the animal cell (a) with the animal cell (b). Examples of usable fusion accelerators are hemagglutinating virus of Japan (HVJ), polyethylene glycol, etc. Further, examples of solvents are water, physiological saline, 5% dimethylsulfoxide aqueous solution, 5% glycerol aqueous solution, etc.

Fusion operation can, for example, be carried out by making the system uniform, in an aqueous medium as above, in the presence of a fusion accelerator as above, if desired with gentle stirring, and then allowing it to stand for a time enough to form a fused cell comprising the animal cell (a) and the animal cell (b), for example for a time of the order of several minutes, and thereby the desired fused cell can be formed.

The resultant system wherein a fused cell was produced is treated, for example by collecting the cells by centrifugation, redispersing the cells in a suitable basal medium. For example when the animal cell (b) has resistance to a drug a medium comprising a basal medium having added thereto the drug is used to redisperse the cells, putting portions of a constant quantity of this dispersion, for example in a 96-well plate for tissue culture, and subjecting it to culture, for example in the presence of 5% $CO_2$ at 37° C. The culture broth in each well is replaced by a fresh medium every three days, culture is continued, for example for 2 weeks, the presence of a fused cell is checked under a microscope, the culture broth of a well wherein a colony was observed is recovered, and the presence of the desired useful substance in the culture broth is detected by an ELISA method.

A colony wherein production of the useful substance was observed is moved to a fresh medium and cultured to proliferate the fused cell, whereby a clone of the fused cell can be obtained. Further, the clone can, if necessary, be subcloned to give a clone excellent in useful substance-producing ability.

The thus recovered fused cell of this invention has a useful substance-producing ability derived from a trait of the animal cell (b), and moreover, can be proliferated (cultured) in passage in a basal medium.

Therefore, the fused cell provided by the method of this invention can be cultured and proliferated in a medium free of expensive calf serum or various growth factors, as is different from the usual case, and thus it is possible to lower culture costs significantly. Further, according to this invention, stable cell culture is possible without adoption of serum or growth factors having an activity changing in each lot, and it is possible to prepare a medium simply and easily without procedures of control, weighing and preparation of various growth factors at the time of preparation of the medium. Further, according to the method of this invention, the medium composition at the time of preparation is apparent, which is different from the case of use of serum containing various unknown nutrient factors, and is simple, and therefore investigation of factors having an influence on proliferation of cells and production of useful substances can readily be carried out. Further, since the resultant fused cell produces the useful substance in the basal medium, the number and quantity of substances other than the useful substance to be removed are overwhelmingly smaller at the time of purification of the useful substance, compared with a medium containing serum or growth factors, and simplification of the purification step is made possible. Thus, the method of this invention has various advantages.

This invention is more specifically described below by examples.

Drawings referred to in the following examples are as follows.

EXAMPLE 1

Cloning of Animal Cell A431 Capable of Proliferating in a Basal Medium

The following cell cloning was carried out to obtain a clone proliferating only in a basal medium from an epidermoid carcinoma-derived cell strain A431 (ATCC CRL 1555).

First, $10^4$ cells of A431 was suspended in 5 ml of DF Medium (DMEM: F-12=1:1) and scattered on Hybridoma Tissue Culture Dish (Greiner Co., Germany, Catalog No 33160). After culture under the condition of 37° C. and 5% $CO_2$ for about one week, proliferation of the cell was observed in about 300 wells. 10 wells wherein particularly good proliferation had been observed were selected, and the contents were moved to a 96-well plate and cultured. Three clones exhibiting particularly good proliferation were selected among them, and their culture scale was enlarged successively to a 24-well plate, a 6-well plate and then a 10-cm dish to proliferate the cells. Parts of them were preserved by freezing, and a proliferation curve was drawn using one clone. This clone is designated A431c.

Figure 1:
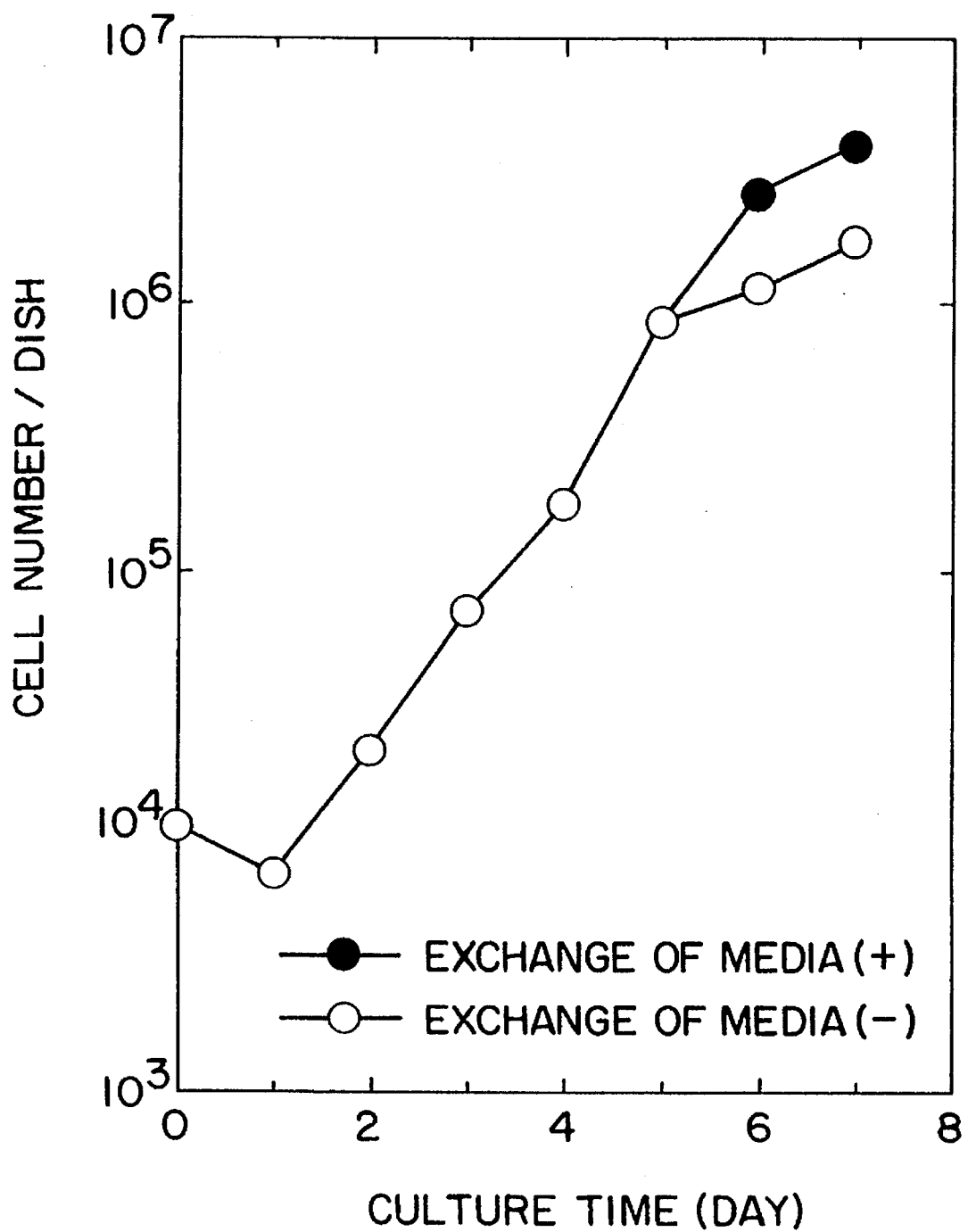
FIG. 1 is a proliferation curve (in DF Medium) OD A431c cloned in Example 1.

A431c was scattered in a tissue-culturing dish of $\emptyset=60$ mm in a quantity of $10^4$ cells per dish, and cultured under the condition of 37° C. and 5% $CO_2$. Measurement of cells was made about every 24 hours. The measurement of cells was made by, after removal of the medium with suction, peeling the cells with PBS containing 0.25% trypsin and 0.02% EDTA, and using a Coulter counter. The results are shown in FIG. 1. After start of the culture, A431c proliferated at a doubling rate of about 15 hours. After culture for 5 days, the medium became yellow and proliferation was discontinued, but proliferation started again by substituting a fresh medium and the cell proliferated up to $2 \times 10^6$ cells to reach confluence.

EXAMPLE 2

Cell Fusion of A431c with TOS/H8 Hybridoma

Cells fusion of A431c obtained in Example 1 with TOS/H8 hybridoma [refer to Hideaki Hagiwara and Junzo Nagao, J. Immunol. Methods, 135, 263–271 (1990)] was carried out. TOS/H8 is a human human hybridoma obtained by cell fusion of a 6-thioguanine- and ouabain-resistant human lymphoblast HIH/TO-1 with a gastric cancer-derived lymphocyte from a human patient, and secretes an IgM monoclonal antibody having a binding affinity against various cancer cell-derived cell strains.

Fusion was carried out in accordance with the method of Hagiwara et al. [Hideaki Hagiwara and Junzo Nagao, J. Immunol. Methods, 135, 263–271 (1990)]. Namely, $1.2 \times 10^7$ cells of A431c at the logarithmic phase and $5.5 \times 10^6$ cells of TOS/H8 are mixed in a 50-ml centrifugal tube and centrifuged at 1500 rpm for 15 minutes. The supernatant was removed, and 1 ml of 50% (v/v) polyethylene glycol 1540 was added dropwise to the cell pellet. Thereafter, DF Medium was added successively in quantities of 1 ml, 2 ml, 4 ml and then 8 ml every two minutes. After centrifugation at 500 rpm for 5 minutes, the supernatant was removed, and 10 ml of DF Medium was gently added and the cell pellet is loosened. Portions of the cell suspension were put in a 96-well plate so as to be 100 μl per well, and cultured under the condition of 37° C. and 5% $CO_2$. After overnight culture, 100 μl of DF Medium containing $10^{-6}$M ouabain was added per well. After further overnight culture, exchange of media was carried out. Namely, 100 μl of the medium was removed and DF Medium containing 100 μl of ouabain was added newly. Then, culture was continued while exchange of media was carried out every 2 to 3 days. After culture of about one month, the cells in all the wells on the 96-well plate were moved to a 24-well plate, and culture was continued. Five clones exhibiting particularly good proliferation in the 24-well plate were selected and subjected to the scale up of culture. Parts of them were preserved by freezing, and one of the clones was subjected to cloning by a limiting dilution method to give 6 clones. One clone which had exhibited best antibody production among them was designated TriH8.

TriH8, which was deposited on Oct. 27, 1993 with the Fermentation Research Institute, Agency of Industrial Science and Technology, located at 1–3 Higashi 1-chome, Tsukuba City, Ibaraki Prefecture 305, Japan, under the terms of the Budapest Treaty, is designated by accession no. FERM BP-4452.

EXAMPLE 3

Proliferation and Antibody Production of TriH8 in a Basal Medium

The quantities of proliferation and antibody production of TriH8 in DF Medium were investigated. TriH8 was inoculated in 30 ml of DF Medium so that the number became $10^5$ cells per ml, and cultured under the condition of 37° C. and 5% $CO_2$. As a control, TOS/H8 was cultured in DF Medium and DF Medium containing 10% FBS for comparision. Sampling of the culture broths and measurement of cell numbers were carried out about every 24 hours. Measurement of cell numbers was carried out using a Coulter counter.

Figure 2:
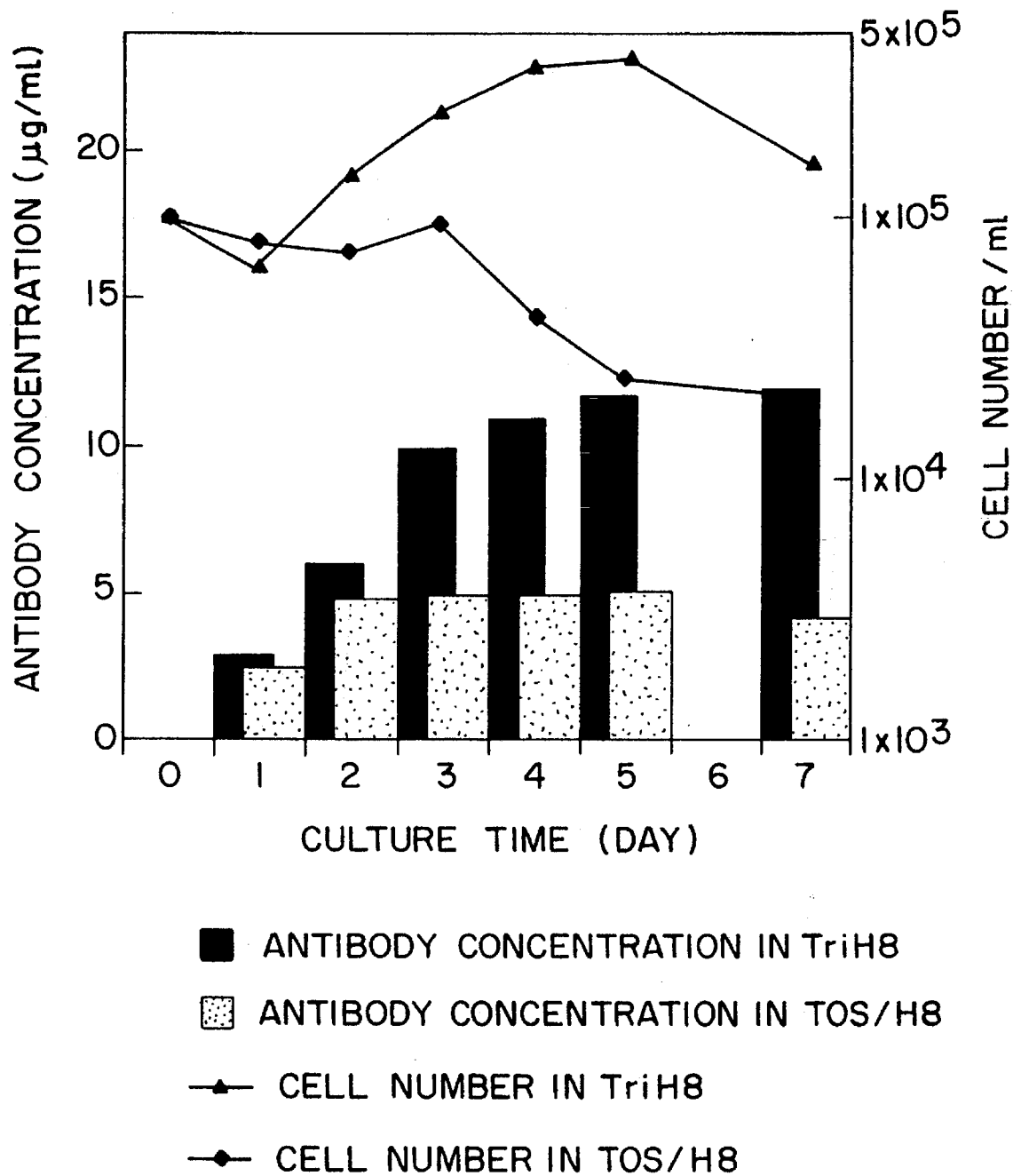
FIG. 2 is a graph showing the proliferation and antibody production quantity of TriH8 and TOS/H8 in DF Medium.

Antibody production quantity was measured by the following method. 100 μl portions of 1 μg/ml an anti-human IgM antibody (Cappel Co.) were put in a 96-well plate for immunoassay (Nunk Co.), and incubation was carried out at 37° C. for 30 minutes. After the wells were washed with phosphate-buffered physiological saline containing 0.3% gelatin (gelatin buffer), blocking was carried out with 1% (w/v) bovine serum albumin. After washing, 50 μl portions of dilutions of standard human IgM and test samples were put therein, and incubated at 37° C. for 1 hour. After washing, 100 μl portions of an anti-human IgM antibody bound to peroxidase (Tago Co.) were put therein, and incubation was carried out at 37° C. for 30 minutes. In the meantime, a substrate solution was prepared. 12 mg of o-phenylenediamine hydrochloride was dissolved in 30 ml of citrate buffer (pH 5.0), and 6 μl of 30% $H_2O_2$ was added to make a substrate solution. After washing, 50 μl portions of the substrate solution were added, and reaction was carried out in a dark place for 15 minutes. 50 μl portions of 5N $H_2SO_4$ were added to stop the reaction, and absorbance at 492 nm was measured using a micro plate reader (Corona Electric Co., Ltd., Japan). Antibody concentrations were determined using a standard curve. The quantities of proliferation and antibody production are shown in FIG. 2. TriH8 proliferates in DF Medium at a doubling time of 30 to 40 hours. TOS/H8 scarcely proliferated in DF Medium. As for antibody production, TriH8 revealed the properties of TOS/H8 both in specificity and production quantity.

Further, it was investigated whether subculture over several generations was possible. TriH8 was inoculated in 30 ml of DF Medium so that the cell concentration became $10^5$ cells/ml, and, after culture of 3 to 4 days, culture was newly started again at $10^5$ cells/ml. This operation was repeated and the antibody production quantity at the time of completion of culture of each generation was measured. As a result, even in case subculture was carried out up to the 25th generation, antibody production lasted without decreasing.

EXAMPLE 4

Cytochemical Analysis of TriH8

(1) Comparison of relative DNA content

In order to confirm whether TriH8 is a cell obtained by fusion of A431 with TOS/H8, comparison of relative DNA content was carried out using a cell sorter.

The cell was fixed with 70% (v/v) ethanol, washed and subjected to RNase treatment at 37° C. for 30 minutes. After washing with distilled water, 50 μg/ml propidium iodide was reacted therewith at room temperature for 20 minutes. After washing with distilled water, the cell was diluted to an appropriate concentration and subjected to analysis by a cell sorter.

Figure 3B:
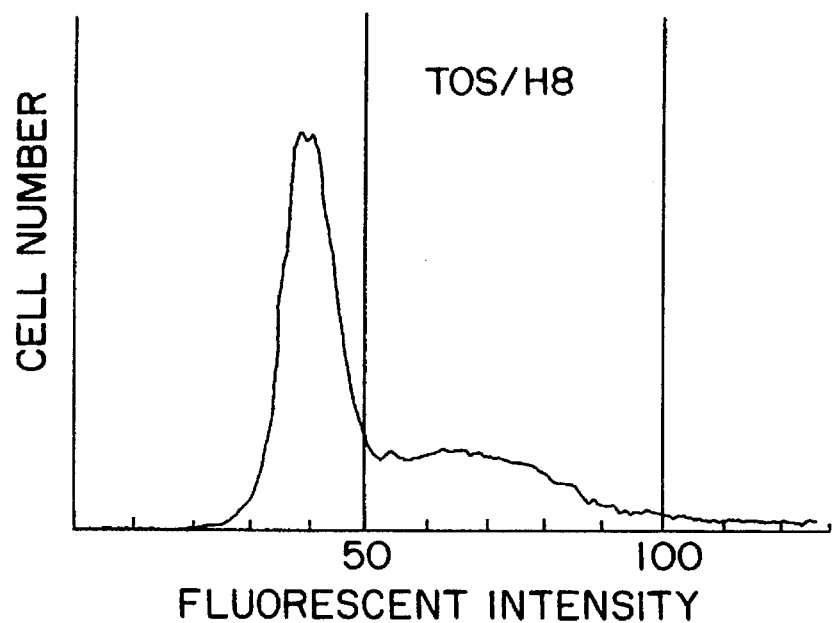
FIGS. 3A and 3B are graphs showing comparison of the relative DNA content of TriH8 and TOS/H8 respectively.
Figure 3A:
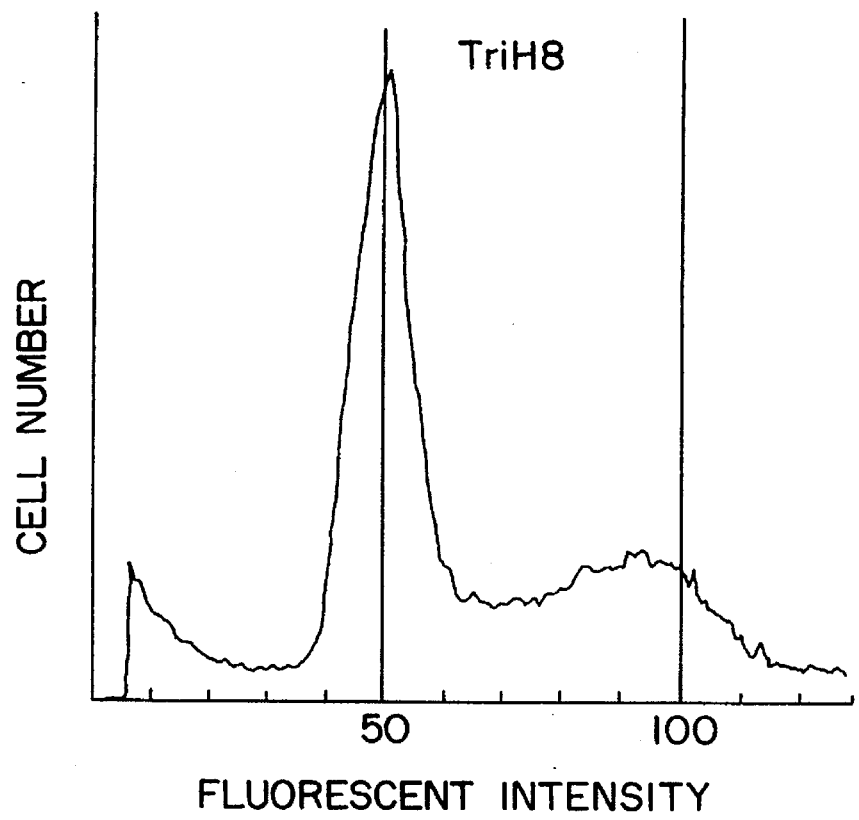

The analytical results on TOS/H8 and TriH8 are shown in FIGS. 3B and 3A, respectively. It is seen that the peak of TriH8 shifts right compared to that of TOS/H8. Namely, it is shown that relative DNA content becomes larger.

(2) Presence of cell surface ECF receptor

It is a well known fact that A431 expresses extraordinarily many EGF (epidermal growth fator) receptors on the cell surface. If TriH8 is a cell obtained by fusion with A431c, EGF receptors ought to exist also on the cell surface of TriH8. Presence of EGF receptors on the cell surface of each of TriH8, TOS/H8 and A431c was checked according to the following method.

First, each cell was washed with DF Medium, and fixed with 3.5% formaldehyde at room temperature for 30 minutes. After washing with PBS, blocking was carried out with 0.5% Skim milk at 37° C. for 30 minutes. After washing, a mouse anti-human EGF receptor antibody (UBI Co.) was reacted therewith at 37° C. for 1 hour. After washing, a goat anti-mouse IgG antibody bound to FITC (fluorescent isothiocyanate) was reacted therewith at 37° C. for 30 minutes. After washing, the cell was observed by a fluorescent microscope. As a result, TOS/H8 was EGF-receptor-negative, while TriH8 was EGF-receptor-positive.

(3) Reactivity with EGF

A431 expresses EGF receptors on the cell surface, and its proliferation is inhibited by addition of EGF to its culture broth [refer to DAVID W. BARNES, J. Cell Biol, 93, 1 (1982)]. It was investigated whether TriH8 obtained by fusion with A431c was influenced by EGF.

A431c and TriH8 were suspended in DF Medium, and portions of each suspension were put in 24-well plates, respectively, so that the cell number became $10^4$ cells per well. Human EGF (UBI Co., No. 01-107) was added thereto to 0 to 10 µg/ml, and culture was started. After culture for 7 days, as for A431c, the culture broth was removed by suction, the cells adhering to the plate were peeled with EDTA-trypsin solution, and the cell number was measured by a Coulter counter. As for TriH8, part of the culture broth was sampled for antibody concentration measurement, and then the cell number was measured by the Coulter counter.

As for A431c, only proliferation of 15% of the control was observed at 5 ng/ml, and almost all the cells were died at 10 ng/ml or more. On the other hand, in case of TriH8, the tendency of proliferation inhibition was observed at 1 µg/ml or more. Thus, the same experiment was carried out with EGF concentrations raised up to 50 µg/ml.

As a control TOS/H8 was used. In TOS/H8, its proliferation in the medium containing serum was scarcely influenced by EGF, whereas in TriH8 the cell number rapidly decreased at 10 µg/ml and proliferation was more inhibited in proportion to increase of the concentration.

We claim:

1. The fused cell line TriH8 having the FRI accession number FERM BP-4452.

* * * * *